United States Patent [19]

Bayer et al.

[11] Patent Number: 5,284,754
[45] Date of Patent: Feb. 8, 1994

[54] PROCESS FOR THE CONTINUOUS CONVERSION OF CEPHALOSPORIN DERIVATIVES INTO GLUTARYL-7-AMINOCEPHALOSPORANIC ACID DERIVATIVES

[75] Inventors: Thomas Bayer; Klaus Sauber, both of Bad Soden am Taunus, Fed. Rep. of Germany

[73] Assignee: Hoechst Aktiengesellschaft, Frankfurt am Main, Fed. Rep. of Germany

[21] Appl. No.: 754,000

[22] Filed: Sep. 3, 1991

[30] Foreign Application Priority Data

Sep. 5, 1990 [DE] Fed. Rep. of Germany ....... 4028119

[51] Int. Cl.$^5$ .............................................. C12P 35/00
[52] U.S. Cl. ........................................ 435/47; 435/25; 435/49; 435/177; 435/178; 435/180; 435/191; 435/174; 435/911
[58] Field of Search ................... 435/47, 25, 191, 911, 435/174, 49, 177, 178, 180

[56] References Cited

U.S. PATENT DOCUMENTS

| | | | |
|---|---|---|---|
| 3,801,458 | 4/1974 | Fildes et al. | 435/47 |
| 3,871,964 | 3/1975 | Huper et al. | 260/112.5 |
| 4,579,818 | 4/1986 | Wolfe et al. | 435/47 |
| 4,906,715 | 3/1990 | Mauz et al. | 526/258 |

FOREIGN PATENT DOCUMENTS

| | | | |
|---|---|---|---|
| 0409521 | 1/1991 | European Pat. Off. | 435/47 |
| 1272769 | 5/1972 | United Kingdom . | |
| 9012110 | 10/1990 | World Int. Prop. O. . | |

OTHER PUBLICATIONS

Jong et al., *ATCC Catalogue of Fungi/Yeasts*, 17th ed., 1987, pp. 429, 427 and 434.
Applied Biochem & Biotech., vol. 27, Issue 3, Dey et al.
Chemical Abstracts, vol. 105, No. 3, Jul. 21, 1986, Abstract #23098P.

*Primary Examiner*—Ronald W. Griffin
*Assistant Examiner*—Pamela S. Webber
*Attorney, Agent, or Firm*—Finnegan, Henderson, Farabow, Garrett & Dunner

[57] ABSTRACT

A process for the continuous conversion of cephalosporin derivatives into glutaryl-7-aminocephalosporanic acid derivatives A process for the continuous conversion of cephalosporin derivatives into the corresponding glutaryl-7-aminocephalosporanic acid derivatives in the presence of a catalyst containing D-amino-acid oxidase is described. The product yield can be increased, where appropriate, by addition of hydrogen peroxide.

21 Claims, No Drawings

PROCESS FOR THE CONTINUOUS CONVERSION OF CEPHALOSPORIN DERIVATIVES INTO GLUTARYL-7-AMINOCEPHALOSPORANIC ACID DERIVATIVES

CephalosporinC (3-acetoxymethyl-7β-(D-5-amino-5-carboxypentanamido)ceph-3-em-4-carboxylic acid) can be oxidized with permeabilized cells of the yeast Trigonopsis variabilis to α-ketoadipinyl-7-aminocephalosporanic acid and subsequently undergo oxidative decarboxylation with hydrogen peroxide to give glutaryl-7-aminocephalosporanic acid (German Offenlegungsschrift 2 219 454). Under the conditions described therein, reaction times of 0.5 to 3 hours are required and a yield of 60 to 73% is achieved.

D-Amino-acid oxidase E.C. 1.4.3.3 (called DAO hereinafter) catalyzes the oxidative deamination of D-amino acids to the corresponding α-keto acids, ammonia and hydrogen peroxide.

Besides commercially available DAO from pig kidneys, the enzyme is synthesized by bacteria, yeasts and fungi. Among these, Trigonopsis variabilis is distinguished as a good DAO producer. Besides the use of this enzyme for racemate resolution of D,L-amino acids and the quantitative detection of D-amino acids in various solutions, particular attention should be drawn to the capacity for oxidative deamination of cephalosporin C.

According to Belgian Patent 736 934, DAO is obtained from fungi and must be released by lysis for the cephalosporin C oxidation which has been mentioned.

German Offenlegungsschrift 2219 454 (U.S. Pat. No. 3 801 458) describes the preparation of cephalosporin C derivatives using activated cells of Trigonopsis variabilis CBS 4095. "Activated" means in this connection that the yeast cells have been subjected to a physical and/or chemical process so that the DAO contained in the cells is made available to catalyze the oxidation of cephalosporin C (CPC) but is not substantially released.

The object of the present invention was to find a process for the substantially complete conversion of cephalosporin derivatives into the corresponding glutaryl-7-aminocephalosporanic acid derivatives in which the known decomposition of cephalosporin in aqueous solutions is substantially prevented, the stability of the DAO-containing catalyst used is improved and a high yield of glutaryl-7-aminocephalosporanic acid (G-7-ACA) is achieved.

A process by which cephalosporin derivatives can be converted into glutaryl-7-aminocephalosporanic acid derivatives has now been found and comprises carrying out the reaction continuously by a DAO-containing catalyst and, where appropriate, subsequently adding hydrogen peroxide.

Surprisingly, by operating the process continuously it has been possible to achieve a substantial improvement in the catalyst utilization by comparison with the "batch" process. Furthermore, the useful life of the DAO-containing catalyst is distinctly increased on continuous addition of the substrates by comparison with the batch process. It has also been possible to reduce the CPC residence time in the reaction vessels.

Thus the invention relates to a process for converting cephalosporin derivatives into the corresponding glutaryl-7-aminocephalosporanic acid derivatives, which comprises carrying out the reaction continuously by a DAO-containing catalyst and, where appropriate, subsequently adding hydrogen peroxide.

It is possible to employ in the process according to the invention all those cephalosporin derivatives which have a D-5-amino-5-carboxypentanamido group on position 7 of the cephalosporin ring. Cephalosporin derivatives of the formula II

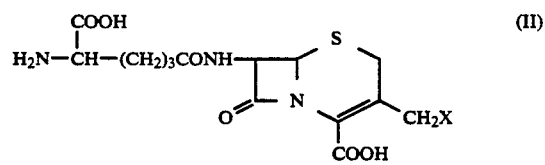

in which X is an acetate group, the radical of a nucleophile, a heterocycle, a hydroxyl group or hydrogen, and salts of cephalosporin derivatives of the formula II, are preferably converted into the connunds of the formula I

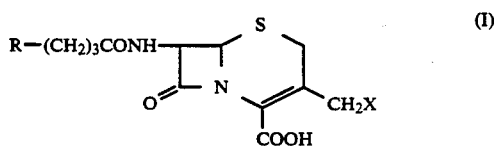

in which X has the abovementioned in a, R is a carboxyl group or a keto carboxyl group, and salts of cephalosporin derivatives of the formula I.

The compounds of the formula II can be employed both in relatively impure state and in prepurified form.

The term nucleophile means, for example, compounds such as pyridine or tertiary amines. The term heterocycle means compounds such as, for example, thiazolyl derivatives, pyrimidines, 6,7-dihydrocyclopenta[b]pyridine, thienyl, pyridyl, pyridazinyl, thiazolinyl, pyrazinyl, indolinyl or indazolyl. Salts of the compounds of the formula I or II are, for example, zinc, ammonium salts or salts of the alkali metals or alkaline earth metals, such as sodium, potassium, calcium or magnesium. The term "DAO-containing catalyst" means immobilized D-amino-acid oxidases, crude enzyme, permeabilized or activated DAO-containing cells, coarsely disrupted DAO-containing cells or isolated purified DAO. The activation or permeabilization is carried out as described in U.S. Pat. No. 3 801 458 or by known physical or chemical methods.

D-amino-acid oxidase (DAO) can be obtained from many organisms, for example from microorganisms, plants, fungi or animal organs such as pig kidney. The DAO from Trigonopsis has proved to be particularly suitable in the process according to the invention. In particular, DAO from Trigonopsis variabilis CBS 4095 can be employed in the process.

The preparation of the DAO from Trigonopsis variabilis is carried out by fermentation as described, for example, in U.S. Pat. No. 3 801 458. The cells are cultured in a complex nutrient medium which contains glucose, yeast extract, potassium phosphate, customary salts and trace elements, and methionine or alanine as nitrogen source.

The DAO can be immobilized as purified enzyme, isolated crude extract, cell extract, in the form of coarsely disrupted cells or together with other enzymes. The Trigonopsis variabilis cells can be disrupted, for example, after cultivation by chemical or physical methods (U.S. Pat. No. 3 801 458) and then immobilized by known processes. For example, immobilization is possible by entrapment in polysaccharides such as, for example, alginate, agar, chitosan or carrageenan or by entrapment in polymers such as acrylic polymer, for example polyacrylamides or crosslinked polyamines. The crosslinked polyamine is preferably an inert protein, such as, for example, albumin or gelatin, which is crosslinked with a di- or polyaldehyde such as glutaraldehyde. It is likewise possible to employ polysaccharides such as chitin or chitosan which are crosslinked with a di- or polyaldehyde or polyphosphate.

Suitable for the immobilization of purified, partially purified or crude cell extracts which contain DAO are, for example, carrier-bound immobilization processes. For example, the DAO can be coupled to the polymeric carrier by a covalent bond via a lysine residue which is not essential for the catalysis. Another possibility is to adsorb the DAO onto a carrier, followed by crosslinking with, for example, glutaraldehyde.

Suitable enzyme carriers are polymeric porous carriers such as celluloses, for example DEAE- or CM-celluloses, Sepharoses such as, for example, Sepharoses activated with BRCN or divinyl sulfone, modified polyacrylamide gels with amino or hydroxyl groups or various organic copolymers of acrylamide, methacrylates or methacrylamide and maleic anhydride. It is also possible furthermore to employ as enzyme carriers copolymers of glycidyl methacrylate, allyl glycidyl ether, methylenebismethacrylamide and methacrylamide such as, for example, ®Eupergit.

Preferred enzyme carriers are crosslinked polymers based on polyvinyl esters and polyvinyl alcohols according to German Offenlegungsschrift 3344 912. The anchoring reaction between DAO and enzyme carrier is carried out in a known manner as described, for example, in DE 2 215 687. The reaction is usually carried out at room temperature or at +40°C. or temperatures below that, in particular at temperatures below +10°C., preferably at 0 to +5° C.

The anchoring reaction is preferably carried out in the vicinity of a neutral pH, for example at pH values from 5 to 9. It is not as a rule necessary, moreover, to maintain more strongly acidic or alkaline conditions because the macroporous bead polymers also react rapidly with the DAO even in the neutral region. The binding resulting therefrom provides sufficient stability for long storage and high operational stability.

The best procedure for the process according to the invention is to pack the DAO-containing catalyst into one, two or more reaction vessels which are connected together and to pass the substrates continuously through the reaction vessel or vessels. The vessels are composed of an inert material which does not react with the substrates and products. The vessels are, for example, stirred tanks, bubble columns or loop reactors and can be enclosed in a cooling/heating jacket. The vessels have inlet and outlet openings for the substrate and product stream and are arranged so that thorough mixing can take place in the reaction vessel. The vessels can be supplied through an additional opening with oxygen or an oxygen-containing gas mixture, for example air, $O_2$-enriched air or nitrogen/oxygen mixtures. The reaction solution can, where appropriate, be mixed with the aid of a stirrer. The reaction vessels are provided with an appropriate retaining device such as, for example, sintered disk, membrane or filter screen whose permeability is chosen substantially to prevent the DAO-containing catalyst from flowing out. The reaction vessels are also provided with appropriate openings to allow disposal of unused gas. Furthermore, the reaction vessels have measurement points for monitoring the course of the reaction, for example measurement of the pH or of the partial pressure of oxygen.

The substrate solution is pumped into the first reaction vessel. This is where the reaction of cephalosporin derivatives with oxygen, catalyzed by DAO, to the corresponding $\alpha$-ketoadipinyl-7-aminocephalosporanic acid derivative, ammonia and hydrogen peroxide takes place. The resulting products and unreacted cephalosporin derivatives can be pumped into the next reaction vessel. This procedure is repeated until the cephalosporin derivatives have been substantially converted. Furthermore, the $\alpha$-ketoadipinyl-7-aminocephalosporanic acid derivative (KA-7-ACA) undergoes oxidative decarboxylation to glutaryl-7-aminocephalosporanic acid with the hydrogen peroxide formed in the reaction vessels. If the KA-7-ACA is not completely converted, it is possible to meter hydrogen peroxide in a controlled manner into a downstream reaction vessel so that the reaction to G-7-ACA takes place substantially completely. Addition of hydrogen peroxide alters the redox potential in the reaction vessel. In continuous operation, the hydrogen peroxide content required for complete conversion can be measured via a redox electrode and kept constant via an appropriate control device by subsequently metering in hydrogen peroxide. This procedure avoids overdosage, which may otherwise result in side reactions such as, for example, oxidation of sulfur.

The cephalosporin derivatives can be added to the reaction mixture in solid form or as solution in water with, where appropriate, additional buffer components. The concentration of the cephalosporin derivatives can vary within wide limits, for example between 0.001 and 1M, preferably between 0.01 and 0.1M. The amount of oxygen introduced can be between 1 and 500 l of $O_2$ per hour and 1 of reaction solution volume, preferably 10 to 100 l of $O_2$ per hour and 1 of reaction solution volume. The DAO concentration employed is between 10 and 5000 units (U) per liter of reaction vessel volume. The DAO-containing catalyst is employed between 0.1 and 95% by weight, preferably 0.5 to 50%, in particular 1 to 20%.

It is advantageous to use a pH between 5 and 9, preferably between 6.0 and 8.5. It is also expedient to carry out the reaction in a temperature range from 4 to 65°C., in particular 10 to 50° C. The most favorable procedure depends on the particular DAO-containing catalyst used and can easily be established in simple preliminary tests.

The residence time of the reaction solution in a vessel can be between 5 min and 800 min, preferably 20 to 120 min. The process can be carried out under sterile or non-sterile conditions.

The reaction products can be converted, after purification or else in the unpurified state, by known chemical or enzymatic conversion into 7-aminocephalosporanic acid (7-ACA). 7-ACA is the starting substrate for a large number of semisynthetic antibiotics.

The invention is explained in more detail hereinafter by means of examples. Percentage data are based on weight.

EXAMPLE 1

Trigonopsis variabilis CBS 4095 is cultivated in the following nutrient solution as preculture:

| | |
|---|---|
| Glucose | 20 g/l (autoclaved separately) |
| D,L-Methionine | 4 g/l (autoclaved separately) |
| KH$_2$PO$_4$ | 2 g/l |
| K$_2$HPO$_4$ | 0.2 g/l |
| MgSO$_4$ × 7H$_2$O | 0.5 g/l |
| CaCl$_2$ × 6H$_2$O | 0.1 g/l |
| NaCl | 0.1 g/l |
| Trace element solution | 10 ml |
| Vitamin solution | 1 ml (add after autoclaving) |
| pH 6.0 | |
| Vitamin solution: | |
| Biotin | 20 mg/l |
| Thiamine | 100 mg/l |
| dissolved in ethanol | (50%) |
| Trace element solution: | |
| Boric acid | 5 g/l |
| MnCl$_2$ × 4H$_2$O | 2 g/l |
| CuCl$_2$ × 3H$_2$O | 2 g/l |
| ZnSO$_4$ × 7H$_2$O | 1 g/l |
| FeCl$_3$ × 6H$_2$O | 3.4 g/l |
| dissolved in double-distilled water | |

An NaCl suspension from slant tubes with an OD$_{578}$ $nm$ = 18 is used as 1% inoculum. Preculturing is carried out at 30° C. and 190 rpm for 24 hours.

The fermentation is carried out under the following conditions:
Nutrient solution:
The nutrient solution corresponds to that for the preculture, but supplemented to the following amounts:

| | |
|---|---|
| Glucose | 30 g/l |
| D,L-Methionine | 6 g/l |
| ® Desmophen | 0.1% (if required) |
| Fermentation conditions: | |
| Inoculum | 2.5–5% |
| Temperature | 28° C. |
| Fermentation time | 50–60 h |

To determine DAO, 0.4 g of cells is frozen, followed by thawing at acidic pH, for example about 3–4; the freezing can take place at a temperature below −10° C., for example about −20° C. Freezing should last sufficiently long to bring about release of DAO from the cells, for example at least 1 hour at −20° C.

The activity is determined by photometry with the following assay mixture:

| Solutions: | |
|---|---|
| 1) Buffer | 100 mM KPP; pH 7.3; air-saturated |
| 2) o-Phenylenediamine | 0.02% in H$_2$O |
| 3) Proxidase | 1 mg/ml in buffer |
| 4) Enzyme | Optimal: 0.5–1.0 unit/ml |
| 5) Substrate | 150 mM Na - CPC (100%) in buffer |
| Assay procedure: | |
| λ = 405 nm (maximum) | |
| ε = 4020 1/mol*cm | |
| ν = 30° C. | |
| Volume: | Final concentration: |
| 1) 2.00 ml | 83 mM |
| 2) 0.50 ml | 0.0034% |
| 3) 0.10 ml | 0.034 mg/ml |
| 4) 0.05 ml | |
| wait for 2 min | |
| 5) 0.30 ml | 15.25 mM |
| 2.95 ml | |

$$\frac{\text{Units}}{\text{ml}} = \frac{\Delta E * \text{dilution} * \text{total volume}}{\text{min} * \epsilon * d * \text{sample volume}}$$

An enzyme activity in the fermenter of 200 U/l is reached under the abovementioned conditions.

EXAMPLE 2

To carry out a heterogeneous crosslinking bead copolymerization, a solution of 80 g of vinyl acetate, 20 g of divinylethyleneurea, 1 g of azoisobutyronitrile and 200 g of n-heptanol was dispersed and polymerized in a solution of 0.175 g of NaH$_2$PO$_4$, 3 g of Na$_2$HPO$_4$ and 5 g of polyvinylpyrrolidone in 500 ml of water. After 4 hours, the diluent was removed by steam distillation and the product was isolated. The yield was 77.7 g of completely round clear bead polymer. The average particle diameter was about 30 μm (stirrer speed 460 rpm).

The product had a bulk volume of 1.55 ml/g. The hydrolyzed product had a bulk volume of 1.54 ml/g and swelled in water to 5 ml/g.

20 g of the hydrolyzed bead copolymer were left to swell in 200 ml of epichlorohydrin at room temperature for 24 hours. Subsequently, while stirring slowly, the temperature was raised to 113 to 115° C. and maintained for 4 hours. After cooling, the copolymer was filtered off through a suction funnel and extracted by stirring in acetone several times for 1 hour each. The acetone-containing copolymer was dried to constant weight in a vacuum oven at 50° C. The epoxide equivalent was 244 (measured by the method of Axen: Acta Chem. Scand. B 29 (1975) No. 4).

EXAMPLE 3

500 μl of a DAO-containing solution (20 U/ml) were added to 100 mg of a carrier prepared as in Example 2. 1 molar potassium phosphate buffer was added to adjust the enzyme solution to pH 7.8. The immobilization of the enzyme on the carrier took 72 hours at 25° C. Subsequently, the DAO which was not covalently bonded to the carrier was removed by suction through a glass frit and the residue was washed several times with 1 molar sodium chloride solution and then with buffer solution. The yield of moist material from the suction filter was 324 mg. The activity was determined as indicated in Example 1 and yielded a value of 18 U/g in the moist state.

EXAMPLE 4

The cells of Trigonopsis variabilis CBS 4095 are cultured and permeabilized by freezing and thawing under the conditions indicated in Example 1. Subsequently, 1 g wet weight of cells is mixed with 10 ml of a 1% strength aqueous chitosan solution and immobilized by adding the mixture dropwise to a 2% strength aqueous sodium tripolyphosphate solution (pH 8.0; 25° C.). A DAO activity of 2.5 U/g wet weight of catalyst is obtained.

EXAMPLE 5

A Enzymatic conversion in a reaction vessel

DAO is immobilized as described in Example 3 and incubated with cephalosporin C in a 1.5 l glass vessel with stirrer and jacket. The following reaction

| | |
|---|---|
| Working volume | 1 l |
| Temperature | 25° C. |

| -continued | |
|---|---|
| DAO concentration | 4% immobilizate (Example 3) 720 U/l |
| Oxygen | 50 l/h |
| pH | 7.0 |
| Cephalosporin C | 30 mM |
| Stirrer speed | 300 rpm |
| Reaction time | 110 min |

After 110 min, 85% of the cephalosporin C employed had been converted. The reaction solution was separated from the immobilized DAO, and the enzyme was provided with fresh substrate solution. After 32 hours, the conversion had fallen to less than 50%.

B Enzymatic conversion into reaction vessels connected in series

DAO is immobilized as described in Example 3 and packed into two 1 l glass vessels with jacket and stirrer. The cephalosporin solution was pumped continuously into the first reaction vessel and passed from there into the second reaction vessel. The following reaction parameters applied:

| Working volume/vessel | 0.5 l |
|---|---|
| Temperature | 25° C. |
| DAO concentration | 4% immobilizate (Example 3) 720 U/l |
| Oxygen | 30 l/h |
| pH | 7.0 |
| Cephalosporin C | 30 mM |
| Stirrer speed | 300 rpm |
| Residence time/vessel | 50 min |
| Total residence time | 100 min |

After 100 min, 85% of the cephalosporin C employed had been converted. Replacement of the catalyst was necessary only after 48 hours because then less than 85% of the cephalosporin employed was converted.

Table 1 shows the comparison of process A with process B according to the invention.

TABLE 1

| | Process A | Process B according to the invention |
|---|---|---|
| Yield | 1.0 | 1.0 |
| Catalyst utilization | 1.0 | 1.5 |
| Reaction time | 1.0 | 0.9 |
| Space-time yield | 1.0 | 1.1 |

We claim:

1. A process for converting a cephalosporin into a glutaryl-7-aminocephalosporanic acid, which comprises continuously reacting the cephalosporin with oxygen in the present of a D-amino-acid oxidase containing catalyst.

2. The process according to claim 1, which further comprises adding hydrogen peroxide during the reaction.

3. The process according to claim 2, wherein said hydrogen peroxide is added continuously.

4. The process according to claim 1, wherein said process comprises the steps of:
   (a) forming a reaction solution comprising a cephalosporin; and
   (b) passing the reaction solution through at least one reaction vessel having therein a D-amino-acid oxidase containing catalyst.

5. The process according to claim 4, wherein the product of steb (b) and any remaining cephalosporin is then passes through at least one more reaction vessel.

6. The process according to claim 4, wherein the product of step (b) and any remaining cephalosporin is then passed through a cascade of reaction vessels until the cephalosporin has been completely converted to the corresponding glutaryl-7-aminocephalosporanic acid.

7. The process according to claim 1, wherein said D-amino-acid oxidase is one derived from fungi.

8. The process according to claim 1, wherein said D-amino-acid oxidase is immobilized with a polysaccharide.

9. The process according to claim 8, wherein said polysaccharide is selected from the group consisting of alginate, carrageenan and chitosan.

10. The process according to claim 1, wherein said D-amino-acid oxidase is immobilized with an enzyme carrier comprising a copolymer selected from the group consisting of polyvinyl ester, polyvinyl alcohol, glycidyl methacrylate, allyl glycidyl ether, methacrylamide and methylenebismethacrylamide copolymers.

11. The process according to claim 1, wherein said D-amino-acid oxidase is immobilized with activated or permeabilized cells.

12. The process according to claim 1, wherein said cephalosporin has the formula II

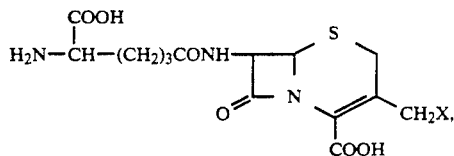

or a salt thereof, wherein X is hydrogen, an acetate group, a nucleophile radical, an hydroxyl group, or a heterocycle, and the resulting glutaryl-7-aminocephalosporanic acid has the formula I

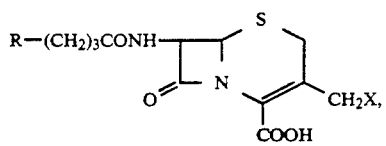

or a salt thereof, wherein X has the same meanings as set forth above, and R is a carboxyl or keto carboxyl group.

13. A process for converting a cephalosporin having the formula II

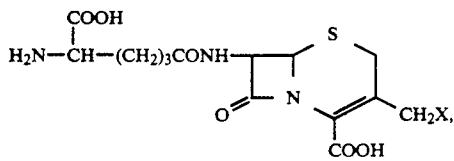

or a salt thereof, wherein X is hydrogen, an acetate group, a nucleophile radical, an hydroxyl group, or a heterocycle, into a glutaryl-7-aminocephalosporanic acid having the formula I

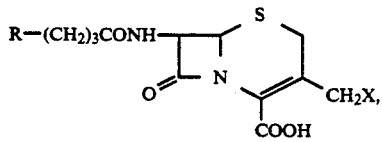

or a salt thereof, wherein X has the same meanings as set forth above, and R is a carboxyl or keto carboxyl group, comprising the steps of:
(a) forming a reaction solution comprising the cephalosporin of formula II; and
(b) continuously reacting the cephalosporin of formula II with oxygen in the presence of a D-amino-acid oxidase containing catalyst, by passing the reaction solution through at least one reaction vessel having therein a D-amino-acid oxidase containing catalyst.

14. The process according to claim 13, which further comprises adding hydrogen peroxide during the reaction.

15. The process according to claim 14, wherein said hydrogen peroxide is added continuously.

16. The process according to claim 13, wherein the product of step (b) and any remaining cephalosporin is then passed through at least one more reaction vessel.

17. The process according to claim 16, wherein the product of step (b) and any remaining cephalosporin is then passes through a cascade of reaction vessels until the cepahalosporin has been completely converted to the corresponding glutaryl-7-aminocephalosporanic acid.

18. The process according to claim 13, wherein said D-amino-acid oxidase is one derived from fungi.

19. The process according to claim 18, wherein said D-amino-acid oxidase is immobilized with a polysaccharide selected from the group consisting of alginate, carrageenan and chitosan.

20. The process according to claim 13, wherein said D-amino-acid oxidase is immobilized with an enzyme carrier comprising a copolymer selected from the group consisting of polyvinyl ester, polyvinyl alcohol, glycidyl methacrylate, allyl glycidyl ether, methacrylamide and methylenebismethacrylamide copolymers.

21. The process according to claim 13, wherein said D-amino-acid oxidase is immobilized with activated or permeabilized cells.

* * * * *

UNITED STATES PATENT AND TRADEMARK OFFICE
CERTIFICATE OF CORRECTION

PATENT NO. : 5,284,754
DATED : February 08, 1994
INVENTOR(S) : Thomas Bayer et al.

It is certified that error appears in the above-indentified patent and that said Letters Patent is hereby corrected as shown below:

Claim 5, column 8, line 2, change "steb" to --step--.

Claim 5, column 8, line 3, change "passes" to --passed--.

Claim 17, column 10, line 7, change "cepahalosporin" to --cephalosporin--.

Signed and Sealed this

Twenty-fifth Day of October, 1994

Attest:

BRUCE LEHMAN

Attesting Officer

Commissioner of Patents and Trademarks